United States Patent
Ah et al.

(10) Patent No.: US 9,493,636 B2
(45) Date of Patent: Nov. 15, 2016

(54) WATER INSOLUBLE GEL COMPOSITION AND METHOD FOR PREPARING SAME

(71) Applicants: Young Chang Ah, Yongin-si (KR); Sung Yeon Cho, Yongin-si (KR); In Seok Hwang, Anseong-si (KR); Sun Young Park, Yongin-si (KR); Hyun Ju Ko, Yongin-si (KR); Hyuk Kim, Yongin-si (KR); Min Jung Kwon, Yongin-si (KR); Won Seok Park, Yongin-si (KR)

(72) Inventors: Young Chang Ah, Yongin-si (KR); Sung Yeon Cho, Yongin-si (KR); In Seok Hwang, Anseong-si (KR); Sun Young Park, Yongin-si (KR); Hyun Ju Ko, Yongin-si (KR); Hyuk Kim, Yongin-si (KR); Min Jung Kwon, Yongin-si (KR); Won Seok Park, Yongin-si (KR)

(73) Assignee: AMOREPACIFIC CORPORATION (KR)

( * ) Notice: Subject to any disclaimer, the term of this patent is extended or adjusted under 35 U.S.C. 154(b) by 109 days.

(21) Appl. No.: 14/359,520

(22) PCT Filed: Nov. 21, 2012

(86) PCT No.: PCT/KR2012/009853
§ 371 (c)(1),
(2) Date: May 20, 2014

(87) PCT Pub. No.: WO2013/077620
PCT Pub. Date: May 30, 2013

(65) Prior Publication Data
US 2014/0331894 A1 Nov. 13, 2014

(30) Foreign Application Priority Data
Nov. 24, 2011 (KR) ........................ 10-2011-0123485

(51) Int. Cl.
C08L 5/08 (2006.01)
A61L 27/20 (2006.01)
A61L 15/28 (2006.01)
(Continued)

(52) U.S. Cl.
CPC .................. *C08L 5/08* (2013.01); *A61L 15/28* (2013.01); *A61L 27/20* (2013.01); *C08B 37/0072* (2013.01); *A61K 9/06* (2013.01); *A61K 47/36* (2013.01); *A61L 2400/06* (2013.01)

(58) Field of Classification Search
None
See application file for complete search history.

(56) References Cited

U.S. PATENT DOCUMENTS 4,937,270 A * 6/1990 Hamilton ............... A61K 47/36
424/488
5,760,200 A * 6/1998 Miller .................. A61K 9/0014
536/119

(Continued)

FOREIGN PATENT DOCUMENTS

KR 1020000012760 3/2000
KR 1020060028604 3/2006

(Continued)

OTHER PUBLICATIONS

Chinese office Action—CN201280057847.2 dated Aug. 4, 2015, citing WO2011-139103.

(Continued)

*Primary Examiner* — Melvin C Mayes
*Assistant Examiner* — Colette Nguyen
(74) *Attorney, Agent, or Firm* — Cantor Colburn LLP (57) ABSTRACT

The present invention provides a method for preparing a water insoluble gel composition comprising: mixing a water soluble polysaccharide, an epoxy cross-linking agent, an alkaline compound and a solvent; and drying the thus obtained mixture at 1 to 30° C. under vacuum to remove the solvent, and a water insoluble gel composition.

13 Claims, 1 Drawing Sheet

(51) Int. Cl.
*C08B 37/08* (2006.01)
*A61K 9/06* (2006.01)
*A61K 47/36* (2006.01)

(56) References Cited

U.S. PATENT DOCUMENTS

| | | | |
|---|---|---|---|
| 6,294,202 B1 * | 9/2001 | Burns | A61L 27/26 424/443 |
| 2004/0127698 A1 * | 7/2004 | Tsai | C08B 37/0072 536/53 |

FOREIGN PATENT DOCUMENTS

| | | |
|---|---|---|
| KR | 1020070004159 | 1/2007 |
| KR | 1020110060257 | 6/2011 |
| KR | 1020110123602 | 11/2011 |
| KR | 1020110123603 | 11/2011 |
| KR | WO2011/139103 * | 11/2011 |
| WO | 2011023355 | 3/2011 |
| WO | 2011139103 | 11/2011 |

OTHER PUBLICATIONS

European Search Report—EP12851320 dated Jul. 13, 2015, citing WO2011-023355, KR2011-0123603, KR2011-0123602 and WO2011-139103.
International Search Report—PCT/KR2012/009853 dated Mar. 29, 2013.

* cited by examiner

WATER INSOLUBLE GEL COMPOSITION AND METHOD FOR PREPARING SAME

TECHNICAL FIELD

The present invention relates to a method for preparing a water insoluble gel composition and a method for preparing the same. More particularly, the present invention relates to a method for preparing a water insoluble gel composition comprising mixing a water soluble polysaccharide, an epoxy cross-linking agent, an alkaline compound and a solvent, and drying the thus obtained mixture at low temperature under vacuum.

BACKGROUND ART

Polysaccharides are natural water soluble polymers having saccharides as repeating units forming them. Since polysaccharides show high viscosity when they are formed into aqueous solution, it is difficult to maintain a high content of polysaccharide contained in a composition, such as lotion, ointment, cream or solution. Such high viscosity makes it difficult to ensure homogeneous mixing of the mixture in a composition. In addition, in the case of a composition to be transplanted to a biotissue, biodegradability is very important. Materials to be transplanted to a biotissue should be non-toxic, and are required to be decomposed and discharged by metabolic actions in vivo after the completion of a desired function. It is known that hyaluronic acid, a typical polysaccharide, is subjected to metabolism and discharged at most 3-4 days after it is implanted or transplanted, regardless of the molecular weight of hyaluronic acid and concentration of hyaluronic acid in a composition. Such a short period of metabolism of hyaluronic acid in vivo makes it inadequate to apply hyaluronic acid not only as a biorestoration material that requires a period of at least several months for the maintenance in vivo but also as a post-surgery tissue anti-adhesion agent that requires a period of about 7-10 days for the maintenance.

When a composition containing a high concentration of polysaccharide is to be formed, one of the problems to be solved is high viscosity occurring when a polysaccharide is dissolved into water. To solve the problem, some methods have been developed and particular examples thereof include a method for reducing the molecular weight of a polysaccharide, a method for increasing the osmotic pressure in aqueous solution, and a method for forming polysaccharide into fine powder, followed by dispersion.

The cross-linking processes developed in order to convert a polysaccharide that is a water soluble polymer into a water insoluble gel may be classified into finding a novel cross-linking agent, controlling the molecular weight of a polysaccharide, controlling the concentration of a polysaccharide in cross-linking reaction solution, controlling the cross-linking density, inducing non-uniformity in cross-linking density, and modifying the type of chemical bonding produced between a polysaccharide and a cross-linking agent.

A general method for converting hyaluronic acid into a water insoluble gel includes mixing hyaluronic acid and an epoxy-based cross-linking agent with water adjusted to pH 12 or higher, and maintaining the mixture at a temperature of about 40-60° C. for several hours. Such a cross-linking process is advantageous in that it accelerates the reaction between the epoxy-based cross-linking agent and hyaluronic acid, but it is disadvantageous in that heating with strong base solution causes a drop in molecular weight of hyaluronic acid, resulting in production of a finished water insoluble gel having excessively low mechanical strength. To compensate for such a drop in molecular weight of hyaluronic acid caused by heating with strong base solution, high-molecular weight hyaluronic acid having a molecular weight of about 3,000,000 Daltons is used instead of currently used hyaluronic acid having a molecular weight of about 1,000,000 Daltons. However, this is not preferred in view of cost efficiency. Another method for solving the problem caused by heating with strong base solution includes reducing pH of hyaluronic acid solution to 12 or lower, or reducing the reaction temperature to below 40° C. However, such methods including reducing pH or reaction temperature are problematic in that an excessively long time is required for cross-linking reaction or an increased amount of cross-linking agent is required. To overcome the disadvantages of cross-linking reaction of hyaluronic acid proceeding in solution, there has been developed a method including incorporating solid state hyaluronic acid into an organic solvent containing an epoxy cross-linking agent dissolved therein. However, the surface of water insoluble gel obtained by the method shows high cross-linking density but the internal portion thereof shows little or no cross-linking density. Another method has been suggested to overcome the disadvantage of a drop in molecular weight of polysaccharide such as hyaluronic acid occurring in the cross-linking reaction proceeding in strong base solution, and the method includes dissolving hyaluronic acid and an epoxy-based cross-linking agent into weakly basic water or distilled water adjusted to pH 9 or less or acidic pH, followed by drying to room temperature. By virtue of the method, it was possible to obtain a hyaluronic acid gel having a weight, after complete swelling, corresponding to at most 2 times of its dry weight even with a very small amount of cross-linking agent. However, after transplanting the water insoluble hyaluronic acid gel obtained by the method to a murine biotissue, 30% of the water insoluble gel was decomposed merely in seven days. Such a degree of biodegradability is not suitable for industrial fields where a water insoluble gel state should be maintained in a tissue in vivo for a long time of several months or more.

DISCLOSURE

Technical Problem

A technical problem to be solved by the present invention which is to provide a novel method for preparing a water insoluble gel composition which maximizes the cross-linking density while minimizing a drop in molecular weight of polysaccharide during the cross-linking step.

Technical Solution

In one general aspect of the present invention, there is provided a method for preparing a water insoluble gel composition, comprising following steps:

mixing a water soluble polysaccharide, an epoxy cross-linking agent, an alkaline compound and a solvent; and drying the thus obtained mixture at 1 to 30° C. under vacuum to remove the solvent.

According to an embodiment of the present invention, the vacuum drying step may be carried out under 1-30 mmHg.

According to another embodiment of the present invention, the step of removing the solvent may be carried out in such a manner that the water soluble polysaccharide is concentrated to a concentration of 50-99 wt %.

According to still another embodiment of the present invention, the water soluble polysaccharide may have a molecular weight of 500,000-5,000,000 Daltons.

According to still another embodiment of the present invention, the water soluble polysaccharide may be used in an amount of 1-100 parts by weight based on 100 parts by weight of the solvent.

According to still another embodiment of the present invention, the water soluble polysaccharide may be at least one selected from the group consisting of hyaluronic acid, hyaluronate, poly-γ-glutamic acid, poly-γ-glutaminate, agar, alginic acid, alginate, carrageenan, furcellaran, pectin, arabic gum, karaya gum, tragacanth gum, ghatti gum, guar gum, locust bean gum, psyllium seed gum, gleatin, chitin, dextran, xanthan gum, chitosan, chondroitin-4-sulfate, chondroitin-6-sulfate and starch.

According to still another embodiment of the present invention, the epoxy cross-linking agent may be used in an amount of 0.01-60 parts by mole per mole of the hydroxyl groups in the water soluble polysaccharide.

According to still another embodiment of the present invention, the epoxy cross-linking agent may be at least one selected from the group consisting of epichlorohydrin, epibromohydrin, 1,4-butandiol diglycidyl ether, ethylene glycol diglycidyl ether, 1,6-hexanediol diglycidyl ether, propylene glycol diglycidyl ether, polyethylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, trimethylpropane polyglycidyl ether, 1,2-(bis(2,3-epoxypropoxy)ethylene, pentaerythritol polyglycidyl ether and sorbitol polyglycidyl ether.

According to yet another embodiment of the present invention, the alkaline compound may be a compound comprising an alkali metal including sodium, potassium, calcium and lithium.

In another general aspect of the present invention, there is provided a water insoluble gel composition comprising a water soluble polysaccharide, an epoxy cross-linking agent, an alkaline compound and a solvent.

According to an embodiment of the present invention, the water soluble polysaccharide may have a molecular weight of 500,000-5,000,000 Daltons.

According to another embodiment of the present invention, the water soluble polysaccharide may be used in an amount of 1-100 parts by weight based on 100 parts by weight of the solvent.

According to still another embodiment of the present invention, the epoxy cross-linking agent may be used in an amount of 0.01-60 parts by mole based on the hydroxyl groups in the water soluble polysaccharide.

According to still another embodiment of the present invention, the composition may comprise 1-20 wt % of the water insoluble gel based on the total weight of the composition.

According to still another embodiment of the present invention, the composition is transparent when the water insoluble gel has a swelling degree of 30-200, is translucent and milky white when the water insoluble gel has a swelling degree of 10-30, and is opaque and white when the water insoluble gel has a swelling degree of 2-10.

According to still another embodiment of the present invention, when the composition is introduced to a phosphate buffer solution having a pH of 6.5-7.5 and swelled and sterilized under pressure, 70-99 wt % of the originally introduced composition remains as a water insoluble gel.

According to yet another embodiment of the present invention, the composition has a weight after swelling corresponding to 2-200 times of the dry weight of the water insoluble gel remaining after the pressure sterilization.

Advantageous Effects

According to the method for preparing a water insoluble gel composition of the present invention, it is possible to obtain a water insoluble gel having excellent strength and stability by using a small amount of cross-linking agent, while minimizing a drop in molecular weight of polysaccharide and maximizing the cross-linking density. When a composition is prepared by using the water insoluble gel, it is possible to ensure the flowability of composition even with an increase in content of polysaccharide in the composition. Therefore, in the fields of cosmetics, health-aid food and pharmaceuticals, it is possible to overcome the problems occurring due to the mixing of a large amount (e.g. 2-3 wt % or more) of polysaccharide, including non-homogeneous mixing during the preparation of composition and degradation of feel in use caused by the loss of flowability during the use of composition. In addition, when a composition consisting of a polysaccharide is transplanted into the body, it is possible to allow the polysaccharide to be retained in vivo stably for at least 10 days to several months. In this manner, the composition may be used as a tissue restoration composition, post-surgery anti-adhesion agent, intra-articular synovia, or the like. Further, the composition is stable against pressure sterilization required essentially for the use as an in vivo transplant material, and has high cost efficiency.

BEST MODE

Preferred embodiments of the present invention now will be described more fully hereinafter so that those skilled in the art may carry out the present invention with ease.

In one aspect, there is provided a method for preparing a water insoluble gel composition, comprising following steps:

mixing a water soluble polysaccharide, an epoxy cross-linking agent, an alkaline compound and a solvent; and drying the thus obtained mixture at 1 to 30° C. under vacuum to remove the solvent.

Hereinafter, the method for preparing a water insoluble gel composition will be explained in more detail.

First, a water soluble polysaccharide, an epoxy cross-linking agent, an alkaline compound and a solvent are mixed.

As used herein, the term 'water soluble polysaccharide' is a water soluble polymer including saccharides as repeating units and having a molecular weight of 500,000 Daltons (Da) to 5,000,000 Da. When the water soluble polysaccharide has a molecular weight less than 500,000 Da, a water insoluble gel is not formed, or even if a water insoluble gel is formed, the gel is extinguished during the pressure sterilization. When the water soluble polysaccharide has a molecular weight larger than 5,000,000 Da, the solution in which the water soluble polysaccharide is dissolved has excessively high viscosity, thereby making it difficult to accomplish homogeneous mixing. A water soluble polysaccharide is a polymer that tends to undergo a drop in molecular weight with ease due to heat, pH and microbial contamination. Therefore, the variable to be considered is the molecular weight, i.e., the final molecular weight, determined after the completion of the steps carried out for cross-linking rather than the molecular weight, i.e. the initial molecular weight, of the polysaccharide introduced as a starting material for cross-linking and washing. Thus, in the present invention, viscosity measurement is carried out to determine a change in molecular weight of the water soluble polysaccharide caused by cross-linking. This is supported by the following test examples.

In general, with regard to cross-linking of a polymer under the same cross-linking density, the swelling degree decreases and the mechanical strength of cross-linked gel increases with an increase in the molecular weight of polymer. The same is also applied to the cross-linking of a polysaccharide. Therefore, when using the same amount of polysaccharide is used for a cross-linking step providing the same cross-linking density, use of a polysaccharide with a higher molecular weight is one of the methods for providing a water insoluble gel at a high yield.

The water soluble polysaccharide is not limited particularly, but particular examples of the water soluble polysaccharide include at least one selected from the group consisting of hyaluronic acid, hyaluronate, poly-γ-glutamic acid, poly-γ-glutaminate, agar, alginic acid, alginate, carrageenan, furcellaran, pectin, arabic gum, karaya gum, tragacanth gum, ghatti gum, guar gum, locust bean gum, psyllium seed gum, gleatin, chitin, dextran, xanthan gum, chitosan, chondroitin-4-sulfate, chondroitin-6-sulfate and starch. Particularly, hyaluronic acid is preferred.

The water soluble polysaccharide is used preferably in an amount of 1-100 parts by weight, more preferably 5-40 parts by weight based on 100 parts by weight of the solvent. When the water soluble polysaccharide is used in an amount less than 1 part by weight, bumping occurs with ease upon drying under vacuum, resulting in degradation of industrial applicability. When the water soluble polysaccharide is used in an amount more than 100 parts by weight, the solution in which the water soluble polysaccharide is dissolved has increased viscosity, thereby making it difficult to accomplish homogeneous mixing.

As used herein, the term 'epoxy cross-linking agent' means a compound comprising at least two epoxy functional groups.

The epoxy cross-linking agent is not limited particularly, and particular examples thereof include at least one selected from the group consisting of epichlorohydrin, epibromohydrin, 1,4-butandiol diglycidyl ether, ethylene glycol diglycidyl ether, 1,6-hexanediol diglycidyl ether, propylene glycol diglycidyl ether, polyethylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, trimethlypropane polyglycidyl ether, 1,2-(bis(2,3-epoxypropoxy)ethylene, pentaerythritol polyglycidyl ether and sorbitol polyglycidyl ether. Particularly, 1,4-butanediol diglycidyl ether (BDDE) is preferred.

The epoxy cross-linking agent may be used in an amount of 0.01-60 parts by mole, preferably 0.05-40 parts by mole, and more preferably 0.1-20 parts by mole per mole of the hydroxyl groups in the water soluble polysaccharide. In other words, the content of epoxy cross-linking agent is determined by the moles of cross-linkable hydroxyl functional groups present in the repeating units forming the water soluble polysaccharide. To control the physical properties of the water insoluble gel of polysaccharide obtained through the cross-linking reaction, the actual amount of reaction between the epoxy cross-linking agent and the polysaccharide during the cross-linking step is important rather than the amount of epoxy cross-linking agent introduced to carry out the cross-linking reaction. Even if a large amount of cross-linking agent is introduced, the portion of cross-linking agent not participating in cross-linking should be removed through a washing step by which the non-reacted cross-linking agent is removed. Therefore, when using the cross-linking agent in an amount within the above-defined range, it is possible to use an optimized amount of cross-linking agent participating actually in cross-linking.

In other words, when the epoxy cross-linking agent is used in an amount less than 0.01 parts by mole, it is not possible to perform cross-linking sufficiently and thus production of a water insoluble gel is hardly possible. When the epoxy cross-linking agent is used in an amount more than 60 parts by mole, cross-linking cannot improve the physical properties of a polysaccharide, the non-reacted cross-linking agent is dangerous, and an increase in cost required for washing causes economical loss.

As used herein, the term 'alkaline compound' is a pH modifier and a general alkaline compound adjusting pH to 12 or higher. The alkaline compound is water soluble and shows a pH of 12 or higher after mixing with water. When a solution in which a polysaccharide and an epoxy-based cross-linking agent are dissolved has a pH of 4 or less, ester bonds are produced largely between hyaluronic acid and the epoxy-based cross-linking agent. When the solution has a pH of 12 or higher, ether bonds are produced largely between hyaluronic acid and the epoxy-based cross-linking agent. When the solution has a pH of 4-12, ester bonds and ether bonds are present in combination between hyaluronic acid and the epoxy-based cross-linking agent. Thus, it is possible to control the type of cross-linking bonds by modifying pH. In the present invention, cross-linking is carried out in an alkaline condition, thereby producing ether bonds. As determined by the following test examples, ether cross-linking bonds are more stable during a pressure sterilization process.

The alkaline compound may be a compound comprising an alkali metal, including sodium, potassium, calcium and lithium. For example, the alkaline compound is preferably sodium hydroxide but is not limited thereto.

Preferably, the solvent is water.

Then, the mixture is dried at 1-30° C. under vacuum to remove the solvent.

This step is carried out by drying the mixture at low temperature under vacuum. As used herein, the low-temperature drying is carried out by drying the mixture under vacuum while controlling the pressure, considering the boiling point of water. Preferably, the temperature of the dried product is maintained at 1-30° C. In addition, the reaction mixture for cross-linking is maintained under a pressure where the boiling point of water is 1-30° C., i.e., a pressure of 1-30 mmHg, while water evaporated from the mixture through drying is removed continuously. After the step of removing the solvent, the water soluble polysaccharide is concentrated to a concentration of 50-99 wt %, preferably 50-90 wt %.

When the temperature is lower than 1° C., the composition obtained after the freeze-drying during the vacuum drying and completion of the drying step becomes porous sponge. Thus, it is not possible to improve the resistance against biodegradation to be sought by the present invention. When the temperature is higher than 30° C., a rapid decrease in molecular weight appears under a strong alkaline condition. Thus, it is difficult to improve the resistance against biodegradation to be sought by the present invention.

In addition, when the pressure is lower than 1 mmHg, the temperature of the composition dried by latent heat of evaporation becomes below the freezing point and the composition is frozen, resulting in a porous sponge structure. Thus, it is difficult to improve the resistance against biodegradation. When the pressure is higher than 30 mmHg, the rate of removal of water is too slow to carry out rapid drying. Thus, an excessively long processing time is required, resulting in degradation of cost efficiency.

While the solvent is removed by such vacuum drying, cross-linking occurs between the water soluble polysaccharide and the epoxy cross-linking agent, thereby forming a water insoluble gel. As a result, it is shown that the vacuum drying step at a low temperature of 30° C. or less inhibits a decrease in molecular weight of water soluble polysaccharide occurring in a strong alkaline aqueous solution state.

As used herein, the water insoluble gel means a three-dimensional network structure formed by cross-linking a water soluble polysaccharide having a linear structure, branched structure with branches attached to the backbone or a radial structure, and has no solubility in water but is merely swelled in water. Main parameters determining the physical properties of the water insoluble gel include the molecular structure and molecular weight of the polymer used for cross-linking, cross-linking density and cross-linking type.

According to the method of the present invention, it is possible to minimize a decrease in molecular weight of polysaccharide occurring during the cross-linking step, to maximize the efficiency of cross-linking between the polysaccharide and the epoxy cross-linking agent, and to maintain a water insoluble gel state stably even under a condition where the water insoluble gel obtained from the cross-linking is mixed with a buffer solution and subjected to pressure sterilization.

In still another aspect of the present invention, there is provided a water insoluble gel composition comprising a water soluble polysaccharide, an epoxy cross-linking agent, an alkaline compound and a solvent.

The composition preferably comprises the water insoluble gel in an amount of 1-20 wt % based on the total weight of the composition. When the water insoluble gel is used in an amount less than 1 wt %, the flowability of the composition is too high to be fixed in a tissue after injection, resulting in degradation of practical applicability. When the water insoluble gel is used in an amount more than 20 wt %, the flowability of the composition is too low to carry out injection using a syringe needle.

The water insoluble gel composition according to the present invention is transparent when it has a swelling degree of 30-200, is translucent and milky white when it has a swelling degree of 10-30, and is opaque and white when it has a swelling degree of 2-10. In general, commercially available compositions containing a hyaluronic acid water insoluble gel are completely transparent. However, the composition containing a water insoluble gel obtained according to the present invention shows different appearance depending on the swelling degree of a hyaluronic acid water insoluble gel in the composition. This results from a different light scattering degree under a lower swelling degree, leading to lower transparency.

When the water insoluble gel composition according to the present invention is introduced to a phosphate buffer solution with a pH of 6.5-7.5 and then swelled and pressure sterilized, 70-99 wt % of the composition based on the weight of the initially introduced composition remains as a water insoluble gel. The phosphate buffer solution preferably has a concentration of phosphate of 0.001M or higher.

As used herein, pressure sterilization is not limited particularly as long as it is generally known to those skilled in the art. For example, pressure sterilization may be carried out at about 121° C. for 20 minutes.

In addition, the composition has a weight after swelling corresponding to 2-200 times of the dry weight of the water insoluble gel remaining after the pressure sterilization. In other words, the weight after swelling of the water insoluble gel remaining after the pressure sterilization and introduced to an isotonic solution for swelling is 2-200 times of the dry weight of the water insoluble gel remaining after the pressure sterilization. When the weight after swelling is less than 2 times of the dry weight, the water insoluble gel has excessively high strength, and thus it is difficult to form the gel into microparticles. On the other hand, when the weight after swelling is larger than 200 times of the dry weight, it is not possible to accomplish the object of improving resistance against biodegradation according to the present invention.

When any one of the functional groups capable of cross-linking present in the cross-linking agent remains unreacted (i.e., cross-linked incompletely), use of a water insoluble gel as a raw material of the composition to be transplanted into a biotissue adversely affects the safety of the transplanted composition. Therefore, according to the present invention, the water insoluble gel subjected to cross-linking is washed and dried again in order to minimize the incompletely cross-linked cross-linking agent in the cross-linked water insoluble gel obtained after the cross-linking. Then, the original water insoluble gel and the water insoluble gel obtained after the redrying step are compared with each other in terms of swelling degree. In this manner, the cross-linking condition under which the incompletely cross-linked cross-linking agent is minimized is optimized.

According to the method for preparing a water insoluble gel composition and the water insoluble gel composition obtained therefrom, it is possible to obtain a water insoluble gel composition having a water soluble polysaccharide of high-molecular weight mixed homogeneously therein by using a small amount of cross-linking agent. The water insoluble gel composition contains a high content of polysaccharide while showing excellent flowability to such a degree that the composition may be injected through a syringe needle. In addition, the water insoluble gel composition is stable against pressure sterilization required essentially when using the composition as an in vivo transplant material, maintains a low swelling degree, and has excellent cost efficiency and quality. Therefore, the water insoluble gel composition according to the present invention may be used in food, cosmetic products, pharmaceuticals and medical instruments as a stabilizer, moisturizer, dispersion aid, viscosity modifier, drug delivery carrier, tissue restoration filler, post-surgery anti-adhesion film-forming material, or the like. More particularly, the water insoluble gel composition may be used as a composition for injection drug carriers, a composition for transmucosal and transdermal absorption drug carriers, a composition for oral drug carriers, a composition for biotissue restoration, a composition for preventing biotissue adhesion after surgery, a filler composition for plastic surgery, an insertion composition for articulation, a patch type wound treatment dressing composition, a composition for treating osteoarthritis, an injection composition for supporting eye surgery, a composition for treating dry eye syndrome, an injection composition for treating wrinkles, a composition for treating gingiva, a composition for treating tympanic membrane perforation, a health-aid food composition or a cosmetic composition.

Examples and Comparative Examples now will be described. The following Examples are for illustrative purposes only and not intended to limit the scope of the present invention.

Comparative Example 1

To a 50 ml capped tube, 1 g of sodium hayaluronate (referred to as HA-Na hereinafter) having a molecular weight of 1,400,000 is introduced. Next, PBS 7.0 is added thereto so that the concentration of HA-Na is 0.5%. Then, the resultant mixture is agitated until a transparent solution is obtained.

Comparative Example 2

To a 50 ml capped tube, 9 g of aqueous sodium hydroxide solution (pH 13) and 1 g of HA-Na having a molecular weight of 1,400,000 are introduced. Next, the resultant mixture is agitated until a transparent solution is obtained. After the completion of the agitation, the resultant mixture is stored in a water bath at 40° C. for 4 hours and diluted with PBS 7.0 to 20 times so that the concentration of HA-Na is 0.5%.

Comparative Example 3

To a 50 ml capped tube, 9 g of aqueous sodium hydroxide solution (pH 13) and 1 g of HA-Na having a molecular weight of 1,400,000 are introduced. Next, the resultant mixture is agitated until a transparent solution is obtained. After the completion of the agitation, the resultant HA-Na solution is placed on a polyethylene plate, pressurized to a thickness of 2 mm and introduced to a heating oven set to 40° C., followed by drying for 24 hours and dilution with PBS 7.0 to a concentration of HA-Na of 0.5%.

Comparative Example 4

To a 50 ml capped tube, 9 g of aqueous sodium hydroxide solution (pH 13) and 1 g of HA-Na having a molecular weight of 1,400,000 are introduced. Next, the resultant mixture is agitated until a transparent solution is obtained. After the completion of the agitation, the resultant HA-Na solution is placed on a polyethylene plate, pressurized to a thickness of 2 mm and dried at room temperature for 4 days, followed by dilution with PBS 7.0 to a concentration of HA-Na of 0.5%.

Comparative Example 5

To a 50 ml capped tube, 9 g of aqueous sodium hydroxide solution (pH 13) and 1 g of HA-Na having a molecular weight of 1,400,000 are introduced. Next, the resultant mixture is agitated until a transparent solution is obtained. After the completion of the agitation, the resultant HA-Na solution is placed on a polyethylene plate, pressurized to a thickness of 2 mm and introduced to a vacuum oven set to 40° C. under a pressure controlled to 10 mmHg or less, followed by drying for 24 hours and dilution with PBS 7.0 to a concentration of HA-Na of 0.5%.

Example 1

To a 50 ml capped tube, 9 g of aqueous sodium hydroxide solution (pH 13) and 1 g of HA-Na having a molecular weight of 1,400,000 are introduced. Next, the resultant mixture is agitated until a transparent solution is obtained. After the completion of the agitation, the resultant HA-Na solution is placed on a polyethylene plate, pressurized to a thickness of 2 mm and introduced to a vacuum oven set to 30° C. under a pressure controlled to 10 mmHg or less, followed by drying for 24 hours and dilution with PBS 7.0 to a concentration of HA-Na of 0.5%.

Test Example 1

Measurement of Viscosity Using Disc Viscometer

The following test is carried out to measure the viscosity of each of the compositions according to Comparative Examples 1-5 and Example 1. The viscosity of a solution containing sodium hyaluronate (molecular weight 1,400,000) in 0.02M phosphate buffer solution (pH 7.0, NaCl 0.8 wt %, referred to as PBS 7.0) at a concentration of 0.5 wt % is measured by using a Brookfield disc viscometer. Viscosity measurement is carried out at a temperature of 25° C. with a disc size #62 under a disc rotation speed of 30 rpm.

The results are shown in the following Table 1. As can be seen from Table 1, the molecular weight of hyaluronic acid shows a rapid drop under a condition using a strong base, when comparing Comparative Examples 1-5 Example 1. It is also found that such a drop in molecular weight of hyaluronic acid occurring in aqueous solution of strong base can be inhibited through a low-temperature vacuum process at 30° C. or lower.

TABLE 1

| | Cross-linking | Hyaluronic acid concentration upon measurement of viscosity (wt %) | Viscosity (cp) |
| --- | --- | --- | --- |
| Comp. Ex. 1 | No cross-linking | 0.5 wt % | 152 |
| Comp. Ex. 2 | Cross-linking in solution/40° C./4 hrs | 0.5 wt % | 12.5 |
| Comp. Ex. 3 | Drying under heating/40° C./24 hrs | 0.5 wt % | 10.8 |
| Comp. Ex. 4 | Room temperature drying/4 days | 0.5 wt % | 10.7 |
| Comp. Ex. 5 | Vacuum drying/40° C./24 hrs | 0.5 wt % | 22.4 |
| Ex. 1 | Vacuum drying/30° C./24 hrs | 0.5 wt % | 47.5 |

Comparative Example 6

To a 50 ml capped tube, 9 g of aqueous sodium hydroxide solution (pH 13), 1 g of HA-Na having a molecular weight of 1,400,000 and 200 mg of BDDE are introduced. Next, the mixture is agitated until a transparent solution is obtained. After the completion of the agitation, the resultant mixture is stored in a water bath for 4 hours and pulverized through a sieve having a mesh size of 1 mm. Cross-linking is carried out in this manner and 1 g of the pulverized sample is introduced to 1000 g of PBS 7.0, followed by agitation for 24 hours.

Example 2

To a 50 ml capped tube, 9 g of aqueous sodium hydroxide solution (pH 13), 1 g of HA-Na having a molecular weight less than 1,400,000 and 200 mg of BDDE are introduced. Next, the mixture is agitated until a transparent solution is obtained. The mixture for cross-linking thus prepared is subjected to vacuum drying for 24 hours in the same manner as Example 1. Then, 0.1 g of the dried mixture for cross-linking is introduced to 1 kg of PBS 7.0, followed by agitation for 24 hours.

Test Example 2

Determination of Cross-Linking Reactivity

The ratio of each cross-linking agent introduced by each cross-linking process of composition according to Comparative Example 6 and Example 2 and participating in cross-linking (i.e., cross-linking reactivity) is evaluated. After completing the agitation of each composition, the supernatant is taken out and unreacted BDDE is determined. After carrying out the cross-linking, the mixture for cross-linking is washed with PBS 7.0. Then, 1,4-butandiol diglycidyl ether (BDDE) contained in PBS 7.0 used for washing is determined by gas chromatography (GC). Neopentyl diglycidyl ether (NPDGE) is used as an internal standard. The determination conditions are described in detail hereinafter.
<Condition for Determination of Unreacted BDDE>
1) Equipment: Agilent 6890GC-5975B MSD
2) GC parameters
  Column: DB-5MS (internal diameter 0.25 mm, length 30 m, coating film thickness 0.25 μm)
  Injector temperature: 260° C.
  Injection mode: He, splitless, purge in 1 min.
  Flow rate of Mobile phase: 1.0 ml/min.
  Injection volume: 1 μl
  Oven temperature: 80° C. 2 min.→warming at 10° C./min.→200° C., 0 min.→warming at 25° C./min.→250° C., 0 min.
3) Mass spectrometer (MS) parameters
  Solvent delay: 8 min.
  Quad temperature: 150° C.
  Source temperature: 250° C.

TABLE 2

| SIM parameters | | | | | |
|---|---|---|---|---|---|
| | Ions (m/z) | | | | |
| | 57 | 71 | 85 | 100 | 127 |
| Dwell time (msec) | 50 | 50 | 50 | 50 | 50 |

The results are shown in the following Table 3. As can be seen from Table 3, in the comparison of Comparative Example 6 with Example 2, the vacuum drying processes provides higher cross-linking reactivity as compared to a solution cross-linking process used generally for cross-linking of polysaccharides. Such higher cross-linking reactivity in a cross-linking process means that introduction of a smaller amount of cross-linking agent can provide a sufficiently cross-linked water insoluble gel.

TABLE 3

| | Cross-linking process | Theoretical BDDE content in sample for GC determination (mg) | Amount of unreacted cross-linking agent (mg) | Cross-linking reactivity (%) |
|---|---|---|---|---|
| Comp. Ex. 6 | Solution cross-linking | 20 | 15.4 | 23 |
| Ex. 2 | Vacuum drying/ 30° C./24 hrs | 200 | 9.5 | 52.5 |

Comparative Examples 7-9

To each of three 50 ml capped tubes, 1 g of HA-Na having a molecular weight of 1,400,000 is introduced, and aqueous HCl solution adjusted to pH 1 by using distilled water and HCl and aqueous sodium hydroxide solution adjusted to pH 12 by using sodium hydroxide are further added each in an amount of 9 g. Then, to each tube, 50 mg of 1,4-butandiol diglycidyl ether (BDDE) is added as a cross-linking agent. After adding BDDE, the mixture is agitated until a transparent solution is obtained, thereby providing a mixture for cross-linking. After the completion of the agitation, vacuum drying is carried out for 24 hours in the same manner as Example 1.

Examples 3-5

To each of three 50 ml capped tubes, 1 g of HA-Na having a molecular weight of 1,400,000 is introduced, and aqueous sodium hydroxide solution adjusted to pH 12.5, 13 and 14 by using sodium hydroxide are further added each in an amount of 9 g. Then, to each tube, 50 mg BDDE is added as a cross-linking agent. After adding BDDE, the mixture is agitated until a transparent solution is obtained, thereby providing a mixture for cross-linking. After the completion of the agitation, pH of the mixture for cross-linking is measured and vacuum drying is carried out for 24 hours in the same manner as Example 1.

Test Example 3

Determination of Stability During Pressure Sterilization

The compositions according to Comparative Examples 7-9 and Examples 3-5 are determined whether they are stable against a pressure sterilization process required essentially when using a water insoluble gel consisting of a polysaccharide.

First, 200 g of each of the compositions dried according to Examples 7-9 and Examples 3-5 is introduced to 200 g of PBS 7.0 and stored for 24 hours. Next, each composition is subjected to pressure sterilization at 121° C. for 15 minutes while it is dipped in PBS 7.0. The pressure sterilization is carried out, after the water insoluble gel is allowed to be swelled completely in phosphate buffer solution. To determine the stability of a water insoluble gel, the water insoluble gel thus pressure sterilized is washed additionally with distilled water, followed by drying, and measured for its weight. In addition, pH of each of the compositions according to Examples 7-9 and Examples 3-5 is measured by using a pH meter. Sterilization stability is calculated by using the following Mathematical Formula 1. The results are shown in the following Table 4.

Sterilization stability (%)=(dry weight of water insoluble gel after pressure sterilization/dry weight of water insoluble gel before pressure sterilization)×100  [Mathematical Formula 1]

Epoxy-based cross-linking agents form a cross-linking bond, depending on pH of solution in which a polysaccharide is dissolved, in the type of ester (acidic pH) or in the type of ether (alkaline pH). As can be seen from Table 4, a mixture for cross-linking obtained by mixing a polysaccharide, an epoxy cross-linking agent, distilled water and a pH modifier should have a pH of 12 or higher to produce a sufficient amount of ether bonds in order to maintain a water insoluble gel even after the pressure sterilization.

TABLE 4

|  | pH of Mixture for cross-linking | Sterilization stability (%) |
|---|---|---|
| Comp. Ex. 7 | 1.04 | 0 |
| Comp. Ex. 8 | 6.4 | 0 |
| Comp. Ex. 9 | 11.6 | 0 |
| Ex. 3 | 12.1 | 91 |
| Ex. 4 | 12.8 | 95 |
| Ex. 5 | 13.5 | 96 |

Comparative Examples 10 and 11

To each of two 50 ml capped tubes, 1 g of HA-Na having a molecular weight of 1,400,000 Da is introduced, and aqueous sodium hydroxide solution adjusted to pH 13 by using sodium hydroxide are further added each in an amount of 9 g. Then, to each tube, BDDE is added as a cross-linking agent in an amount of 0.1 mg (0.02 mol %) and 300 mg (60 mol %). After adding BDDE, the mixture is agitated until a transparent solution is obtained, thereby providing a mixture for cross-linking. After the completion of the agitation, vacuum drying is carried out for 24 hours in the same manner as Example 1. Next, the dry mixture for cross-linking is introduced to 200 g of PBS 7.0, and stored for 24 hours. Then, it is determined whether a water soluble gel is present or not.

Examples 6-9

To each of four 50 ml capped tubes, 1 g of HA-Na having a molecular weight of 1,400,000 Da is introduced, and aqueous sodium hydroxide solution adjusted to pH 13 by using sodium hydroxide are further added each in an amount of 9 g. Then, to each tube, BDDE is added as a cross-linking agent in an amount of 0.25 mg (0.05 mol %), 0.5 mg (0.1 mol %), 50 mg (10 mol %) and 200 mg (40 mol %). After adding BDDE, the mixture is agitated until a transparent solution is obtained, thereby providing a mixture for cross-linking. Vacuum drying is carried out for 24 hours in the same manner as Example 1. Next, the dry mixture for cross-linking is introduced to 200 g of PBS 7.0, stored for 24 hours, and subjected to pressure sterilization at 121° C. for 15 minutes while it is dipped in PBS 7.0. Then, to determine the stability of a water insoluble gel, each pressure sterilized water insoluble gel is washed additionally with distilled water and dried, and then the weight of each water insoluble gel is measured.

Test Example 4

Determination of Physical Properties Depending on Introduction Amount of Cross-Linking Agent To determine the maximum and minimum of the introduction amount of a cross-linking agent, comparison is made among Comparative Examples 10 and 11 and Examples 6-9. The introduction amount of a cross-linking agent and the yield of a gel are calculated according to the following Mathematical Formulae 2 and 3, respectively. The results are shown in the following Table 5. As a result, it is shown that an epoxy-based cross-linking agent is introduced suitably in an amount of 0.05-40 mol % based on cross-linking density in view of the low-temperature vacuum drying process. As the introduction amount of a cross-linking agent increases, the yield of a gel decreases rather and the mechanical strength of a water insoluble gel decreases, suggesting that the epoxy-based cross-linking agent forms cross-linking bonds but has an effect of cleaving the molecular chain of a polysaccharide at the same time.

Introduction amount of cross-linking agent (mol %)= [(Number of epoxy functional groups in cross-linking agent×Introduction amount of cross-linking agent (g)/Molecular weight of cross-linking agent (g/mol))/(Number of hydroxyl functional groups capable of bonding in repeating units of water soluble polymer×Introduction amount of polysaccharide (g)/Molecular weight of polysaccharide repeating units (g/mol))×100  [Mathematical Formula 2]

Yield of gel (%)=(Weight of charged polysaccharide/ Weight of polysaccharide in the resultant water insoluble gel)×100  [Mathematical Formula 3]

TABLE 5

|  | Amount of cross-linking agent (mol %) | Yield of gel (%) | Sterilization stability (%) | Swelling degree after pressure sterilization |
|---|---|---|---|---|
| Comp. Ex. 10 | 0.02 | 0 | 0 | 0 |
| Comp. Ex. 11 | 60 | 0 | 0 | 0 |
| Ex. 6 | 0.05 | 5 | 0 | 0 |
| Ex. 7 | 0.1 | 24 | 50 | Not available(*) |
| Ex. 8 | 10 | 98 | 94 | 6.2 |
| Ex. 9 | 40 | 25 | Not available | Not available |

(*)The mechanical strength of a water insoluble gel is too low to measure the resistance against pressure sterilization and swelling degree.

Comparative Examples 12-15

To each of four 50 ml capped tubes, 1 g of HA-Na having a molecular weight of 1,400,000 Da is introduced, and 9 g of aqueous sodium hydroxide solution adjusted to pH 13 by using sodium hydroxide and 10 mg (2 mol %) of BDDE as a cross-linking agent are further added. Then, the mixture is agitated until a transparent solution is obtained, thereby providing a mixture for cross-linking. After the completion of the agitation, each of the mixture for cross-linking contained in a different tube is subjected to vacuum drying in the same manner as Example 1. Herein, during the vacuum drying, the mixture for cross-linking is taken out one by one sequentially in one-hour intervals from the beginning time of the drying and divided into two portions. One portion is used to measure the water content, while the other portion is dipped in 50 g of PBS 7.0 and stored therein for 24 hours. The sample dipped in PBS 7.0 is observed by the naked eyes to determine whether a water insoluble gel is formed or not, and pressure sterilized at 121° C. for 15 minutes still in PBS 7.0. To determine the stability of a water insoluble gel, each pressure sterilized water insoluble gel is washed additionally with distilled water and dried, and then the weight of each water insoluble gel is measured.

Examples 10-15

To each of six 50 ml capped tubes, 1 g of HA-Na having a molecular weight of 1,400,000 Da is introduced, and 9 g of aqueous sodium hydroxide solution adjusted to pH 13 by using sodium hydroxide and 10 mg (2 mol %) of BDDE as a cross-linking agent are further added. Then, the mixture is agitated until a transparent solution is obtained, thereby providing a mixture for cross-linking. After the completion of the agitation, each of the mixture for cross-linking contained in a different tube is subjected to vacuum drying in the same manner as Example 1. Herein, during the vacuum drying, the mixture for cross-linking is taken out one by one sequentially in one-hour intervals from the time of 5 hours after beginning the drying and divided into two portions. One portion is used to measure the water content, while the other portion is dipped in 50 g of PBS 7.0 and stored therein for 24 hours. The sample dipped in PBS 7.0 is observed by the naked eyes to determine whether a water insoluble gel is formed or not, and pressure sterilized at 121° C. for 15 minutes still in PBS 7.0. To determine the stability of a water insoluble gel, each pressure sterilized water insoluble gel is washed additionally with distilled water and dried, and then the weight of each water insoluble gel is measured.

Test Example 5

Measurement of Water Content Depending on Drying Time

During the cross-linking of the compositions according to Comparative Examples 12-15 and Examples 10-15 through the low-temperature vacuum drying, cross-linking efficiency is evaluated as a function of cross-linking time in order to determine a suitable cross-linking time. For this, each sample prepared for each time of low-temperature vacuum drying is introduced to a heat-sensitive weighing system to measure the water content. Measurement is carried out by measuring a change in weight at 105° C. in 5-minute intervals for 3 hours. The results are shown in the following Table 6.

It can be seen that the content of water contained in a mixture for cross-linking is a more important factor as compared to cross-linking time in the low-temperature vacuum drying process. It can be also seen that a period of 1 hour or more is maintained suitably after the water content in a mixture for cross-linking becomes 20% or less.

TABLE 6

| | Drying time | Water content (%) | Yield of gel (%) | Sterilization stability (%) | Swelling degree after pressure sterilization |
|---|---|---|---|---|---|
| Comp. Ex. 12 | 1 | 87 | 0 | 0 | — |
| Comp. Ex. 13 | 2 | 61 | 0 | 0 | — |
| Comp. Ex. 14 | 3 | 42 | 0 | 0 | — |

TABLE 6-continued

| | Drying time | Water content (%) | Yield of gel (%) | Sterilization stability (%) | Swelling degree after pressure sterilization |
|---|---|---|---|---|---|
| Comp. Ex. 15 | 4 | 24 | 0 | 0 | — |
| Ex. 10 | 5 | 15 | 65 | 74 | 25 |
| Ex. 11 | 6 | 12 | 88 | 85 | 15 |
| Ex. 12 | 7 | 8 | 94 | 94 | 9.5 |
| Ex. 13 | 8 | 8 | 95 | 95 | 8.9 |
| Ex. 14 | 9 | 7 | 96 | 95 | 9.2 |
| Ex. 15 | 10 | 6 | 97 | 96 | 9.0 |

Comparative Examples 17 and 18

To each of two 50 ml capped tubes, 4 g of aqueous sodium hydroxide solution adjusted to pH 13 by using sodium hydroxide is introduced, and then HA-Na having a molecular weight of 1,400,000 Da is further added thereto each in an amount of 20 mg and 6 g. No cross-linking agent is introduced to the sample to which 20 mg of HA-Na is introduced. In addition, 60 mg (2 mol %) of BDDE is introduced to the sample (Comparative Example 18) using 6 g of HA-Na as a cross-linking agent, followed by agitation. In the case of the sample using 6 g of HA-Na, it is not possible to obtain a transparent solution. After the completion of the agitation, each sample is subjected to vacuum drying in the same manner as Example 1. After the vacuum drying, each sample is introduced to PBS 7.0 and stored therein for 24 hours.

Examples 16-22

To each of seven 50 ml capped tubes, 4 g of aqueous sodium hydroxide solution adjusted to pH 13 by using sodium hydroxide is introduced, and then HA-Na having a molecular weight of 1,400,000 Da is further added thereto each in an amount of 200 mg, 400 mg, 600 mg, 800 mg, 1.6 g and 4 g, followed by agitation. After the completion of the agitation, each sample is subjected to vacuum drying in the same manner as Example 1. After the vacuum drying, each sample is introduced to PBS 7.0 so that the concentration of HA-Na is 0.5 wt %. After HA-Na is dissolved completely, viscosity measurement is carried out by using a disc viscometer. In Example 22, after the completion of the drying, the sample is introduced to PBS 7.0, agitated for 24 hours, subjected to pressure sterilization at 121° C. for 15 minutes, washed with distilled water and dried again.

Test Example 6

Determination of Physical Properties Depending on Introduction Amount of Water Soluble Polysaccharide The introduction amount of a water soluble polysaccharide in each of the compositions according to Comparative Examples 17 and 18 and Examples 16-22 is measured. When a polysaccharide is maintained at a high concentration in a process for preparing a water insoluble gel through the cross-linking of the polysaccharide, it is possible to reduce the water content in the mixture for cross-linking, and thus to increase the cross-linking reaction rate.

The results are shown in the following Table 7. It can be seen from Comparative Example 18 that an excessively high concentration of polysaccharide in the mixture for cross-linking causes a drop in yield of water insoluble gel. It is though that this results from poor mixing homogeneity between the polysaccharide and the cross-linking agent in the mixture for cross-linking due to the use of an excessively high concentration of polysaccharide. On the contrary, reducing the concentration of polysaccharide in the mixture for cross-linking agent to facilitate homogeneous mixing also has a disadvantage. It can be seen from Comparative Example 17 that addition of an excessively low concentration of polysaccharide to obtain a low-viscosity mixture for cross-linking provides a drop in molecular weight of NA-Na in a similar manner to the conventionally used solution cross-linking process. It can be also seen from Examples 16-22 that 1-100 parts by weight, practically 5-66 parts by weight of polysaccharide is used suitably in the reaction of polysaccharide, based on 100 parts by weight of aqueous strong base solution as a solvent for dissolving the polysaccharide.

TABLE 7

| | HA concentration (parts by weight*) | Introduction amount of cross-linking agent (mol %) | Viscosity after low-temperature vacuum drying (0.5 wt %, cp) | Yield of gel (%) |
|---|---|---|---|---|
| Comp. Ex. 17 | 0.5 | 0 | 12.5 | Not available |
| Ex. 16 | 1 | 0 | 18 | |
| Ex. 17 | 5 | 0 | 25 | |
| Ex. 18 | 10 | 0 | 47.5 | |
| Ex. 19 | 15 | 0 | 55 | |
| Ex. 20 | 20 | 0 | 66 | |
| Ex. 21 | 40 | 0 | 72 | |
| Ex. 22 | 100 | 0 | 77 | |
| Comp. Ex. 18 | 150 | 2 | Not available | 34 |

Comparative Examples 19-23

To 50 ml capped tubes, HA-Na having a molecular weight of 7,100 Da, 83,000 Da, 420,000 Da and 1,400,000 Da on the basis of number average molecular weight is introduced as shown in the following Table 8. Next, 9 g of aqueous sodium hydroxide solution adjusted to pH 13 by using 1 g of sodium hydroxide and 10 mg (2 mol %) of BDDE are added thereto, followed by mixing and agitation. When the mixture for cross-linking becomes completely transparent after the completion of the agitation, vacuum drying is carried out for 24 hours in the same manner as Example 1. After the vacuum drying, each sample is introduced to PBS 7.0, followed by agitation for 24 hours. After washing with PHS 7.0 for 24 hours, the presence of a water insoluble gel is determined by the naked eyes. Then, each sample is pressure sterilized at 121° C. for 15 minutes, washed with distilled again, and dried again.

Example 23

In a 50 ml capped tube, 0.5 g of HA-Na having a molecular weight of 420,000 on the basis of number average molecular weight, 0.5 g of HA-Na having a molecular weight of 1,400,000 on the basis of number average molecular weight, 9 g of aqueous sodium hydroxide solution adjusted to pH 13 by using sodium hydroxide and 10 mg (2 mol %) of BDDE are mixed and agitated. When the mixture for cross-linking becomes transparent completely, vacuum drying is carried out in the same manner as Example 1. After the completion of the drying, the mixture is agitated until it is transparent completely. When the mixture for cross-linking becomes completely transparent after the completion of the agitation, vacuum drying is carried out for 24 hours in the same manner as Example 1. After the vacuum drying, each sample is introduced to PBS 7.0, followed by agitation for 24 hours. After washing with PHS 7.0 for 24 hours, the presence of a water insoluble gel is determined by the naked eyes. Then, each sample is pressure sterilized at 121° C. for 15 minutes, washed with distilled again, and dried again.

Test Example 7

Determination of Physical Properties Depending on Molecular Weight of Water Soluble Polysaccharide For the compositions according to Comparative Examples 19-23 and Example 23, the yield of a gel is determined as a function of molecular weight of polysaccharide.

In the case of hyaluronic acid, hyaluronic acid having a molecular weight of about 1,000,000 Da is applied generally to cross-linking. To compensate for a drop in molecular weight occurring during the cross-linking, hyaluronic acid having a molecular weight of several millions Da or more may be applied to cross-linking. However, such a method causes an increase in cost and makes it difficult to ensure the mixing homogeneity during the preparation of a mixture due to high viscosity.

On the contrary, a range of molecular weights suitable for preparation of a water insoluble gel has not been found yet in the case of a polysaccharide having a low molecular weight. According to the present invention, it can be seen from Comparative Examples 19-23 and Example 23 that HA-Na having a number average molecular weight of 420,000 Da or less cannot provide a water insoluble gel even after being subjected to cross-linking, or if any, a water insoluble gel is extinguished during the pressure sterilization, resulting in a limitation in its application range. Therefore, when carrying out cross-linking through a low-temperature vacuum drying process, it is required for a polysaccharide to have a number average molecular weight of 500,000 Da or more.

TABLE 8

| | Injection amount of HA-Na (g) defined by number average molecular weight | | | | Yield of gel (%) | Sterilization stability (%) | Swelling degree after sterilization |
|---|---|---|---|---|---|---|---|
| | 7,100 Da | 83,000 Da | 420,000 Da | 1,400,000 Da | | | |
| Comp. Ex. 19 | 1.0 | 0 | 0 | 0 | 0 | 0 | Not available |
| Comp. Ex. 20 | 0 | 1.0 | 0 | 0 | 0 | 0 | Not available |
| Comp. Ex. 21 | 0 | 0 | 1.0 | 0 | 85 | 0 | Not available |
| Comp. Ex. 22 | 0.5 | 0 | 0 | 0.5 | 81.6 | 0 | Not available |
| Comp. Ex. 23 | 0 | 0.5 | 0 | 0.5 | 85.3 | 0 | Not available |
| Ex. 23 | 0 | 0 | 0.5 | 0.5 | 96 | 75 | 180 times or higher |

Test Example 8

Determination of Physical Properties Depending on Molecular Weight of Water Soluble Polysaccharide In this test example, the composition according to Example 11 is used. Herein, after the low-temperature vacuum drying, the unreacted cross-linking agent and NaOH are removed by using PBS 7.0 and distilled water, followed by redrying. As the references for comparison, commercially available products containing cross-linked hyaluronic acid, including Perlane [reference 1(P)] available from Q-med, Juvederm-Ultra [reference 2(J-U)] available from Allergane, Esthelis Basis [reference 3(E-B)] available from Antheis, and Glytone-2 [reference 4(G-2)] available from PFDC are used. Each commercially available product is obtained by way of a hospital for the purpose of study.

The redried water insoluble gel is pulverized to obtain powder having a size of 100 μm or less. The water insoluble gel in the form of powder is mixed with PBS 7.0 to a content of water insoluble gel of 5 w/v %. To a glass-made prefilled syringe having an internal volume of 1 ml, the composition of PBS 7.0 mixed with the water insoluble gel is introduced. Then, the syringe is sealed with a rubber-made stopper and subjected to pressure sterilization at 121° C. for 15 minutes. The pressure applied when the pressure sterilized composition is ejected through a syringe needle with a size of 27½G and the enzymolysis resistance after sterilization are observed.

8-1. Determination of Injection Quality

A tensile tester is set in a compression strength measuring mode to determine injection quality. A syringe containing composition comprising hyaluronic acid gel therein is decapped and a syringe needle with a size of 27½G is mounted thereto. Next, the syringe is fixed vertically on the plate of the tensile tester with the syringe needle side down. The tensile tester is operated to push the plunger mounted to the syringe at a rate of 1 mm/sec and the force against compression is measured until the content in the syringe is removed completely.

8-2. Determination of Resistance Against Enzymolysis

A hyaluronic acid composition sterilized under pressure is taken in an amount of 5 mg as hyaluronic acid and mixed with 0.5 ml of a solution containing 200 IU/ml of hyaluronidase dissolved therein in such a manner that 20 IU of hyaluronisase is mixed per milligram of hyaluronic acid. After the mixing, the mixture is stored at 37° C. for 8 hours. After 8 hours, 4 ml of 0.1N HCl solution is added to quench the enzymolysis and agitation is carried out vigorously. Then, distilled water is added thereto to a total volume of 10 ml. After the mixture is agitated for one day so that non-cross-linked hyaluronic acid is dissolved out, the mixture is subjected to centrifugal separation under 3000 rpm for 20 minutes and the supernatant is taken. The hyaluronic acid contained in the supernatant is determined and the degree of enzymolysis is calculated according to the following Mathematical Formula 4.

Resistance against enzymolysis (%)={(Content of cross-linked hyaluronic acid gel before the introduction of enzyme (mg)−Concentration of hyaluronic acid in the supernatant measured after the introduction of enzyme (mg/ml)×10 (ml))/Content of cross-linked hyaluronic acid gel before the introduction of enzyme (mg)}× 100       [Mathematical Formula 4]

The results are shown in the following Table 9. As can be seen from Table 9, the composition according to the present invention shows a hyaluronic acid content of 5%, which is 2.5 times higher than the hyaluronic acid content (2%) of the commercially available product. However, the composition according to the present invention provides injection quality at least equal to the injection quality of the commercially available products. In addition, the composition according to the present invention provides excellent resistance against enzymolysis in the above-described enzymolysis test. Thus, it is shown that the composition can provide a longer retention time in a biotissue after it is transplanted in the biotissue.

TABLE 9

| Products | Injection quality (N) | Resistance against enzymolysis (%) |
|---|---|---|
| Ex. 11 | 25 ± 2 | 68 |
| Commercially available product 1 (P) | 24 ± 1 | 39.5 |
| Commercially available product 2 (J-U) | 31 ± 2 | 23.2 |
| Commercially available product 3 (E-B) | 33 ± 5 | 0 |
| Commercially available product 4 (G-2) | 31 ± 7 | 0 |

Test Example 9

Maintenance Quality of Hyaluronic Acid Water Insoluble Gel in Biotissue

Figure 1:
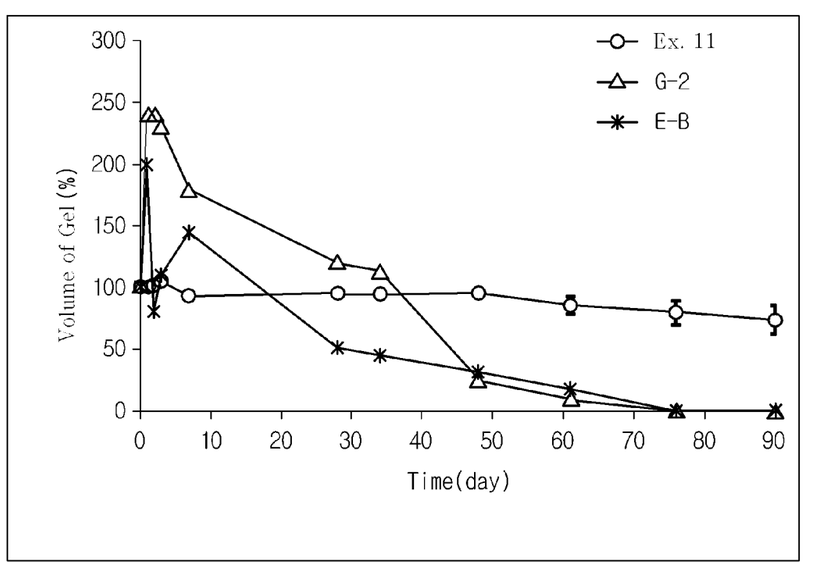
FIG. 1 is a graph illustrating the volume retaining period of the hyaluronic acid composition according to an embodiment of the present invention.

Each of the same compositions used in Test Example 8 are injected to the back portion of a hairless mouse and the volume maintenance period is observed. Herein, 0.2 ml of each hyaluronic acid water insoluble gel composition sterilized under pressure is injected to the back portion of a hairless mouse and variations in volume are observed for three months. The results are shown in FIG. 1. As can be seen from FIG. 1, after injecting the composition according to the present invention to the back portion of a hairless mouse, an improved volume maintenance effect is obtained as compared to the commercially available products.

Examples 24-29

To 50 ml capped tubes, HA-Na having a molecular weight of 1,400,000 Da is introduced in an amount of 1 g, and 9 g of aqueous sodium hydroxide solution adjusted to pH 13 by using sodium hydroxide and BDDE as a cross-linking agent are added thereto as shown in the following Table 10. Next, the mixture is agitated until a transparent solution is obtained, thereby providing a mixture for cross-linking. After the completion of the agitation, vacuum drying is carried out in the same manner as Example 1. Then, the dried mixture for cross-linking is introduced to PBS 7.0 and agitated for 24 hours, and washed again by way of agitation in distilled water, and dried again.

Test Example 10

Appearance of Composition

The transparency of each of the compositions according to Example 11 and Examples 23-29 is observed. Each water insoluble gel is pulverized in its dry state to 100 μm and mixed with PBS 7.0 to be swelled completely. Then, the mixture is subjected to centrifugal separation and the supernatant is removed. The remaining water insoluble gel is filled into a 1 ml glass syringe, sterilized under pressure, and the appearance of the gel is observed by the naked eyes. The results are shown in the following Table 10.

TABLE 10

| | Molecular weight of HA-Na (Number average/Da) | Introduction amount of cross-linking agent (mol %) | Swelling degree after sterilization | Appearance |
|---|---|---|---|---|
| Ex. 11 | 1,400,000 | 2 | 180 times or more | Transparent |
| Ex. 23 | 900,000 | 2 | 15 | Translucent |
| Ex. 24 | 1,400,000 | 0.1 | 75 times or more | Transparent |
| Ex. 25 | 1,400,000 | 0.5 | 28 | Translucent |
| Ex. 26 | 1,400,000 | 4 | 8.8 | Opaque |
| Ex. 27 | 1,400,000 | 8 | 7.1 | Opaque |
| Ex. 28 | 1,400,000 | 16 | 5.4 | Opaque |
| Ex. 29 | 1,400,000 | 20 | 3.5 | Opaque |

The invention claimed is:

1. A method for preparing a water insoluble gel composition, comprising the following steps:
   mixing a water soluble polysaccharide, an epoxy cross-linking agent, an alkaline compound and water; and
   drying the thus obtained mixture at 1 to 30 C under vacuum to remove the water, wherein the drying is carried out at 1-30 mmHg thereby forming the water insoluble gel composition through cross-linking between the water soluble polysaccharide and the epoxy cross-linking agent.

2. The method for preparing a water insoluble gel composition according to claim 1, wherein the step of removing the water is carried out in such a manner that the water soluble polysaccharide is concentrated to a concentration of 50-99 wt %.

3. The method for preparing a water insoluble gel composition according to claim 1, wherein the water soluble polysaccharide has a molecular weight of 500,000-5,000,000 Daltons.

4. The method for preparing a water insoluble gel composition according to claim 1, wherein the water soluble polysaccharide is used in an amount of 1-100 parts by weight based on 100 parts by weight of the water.

5. The method for preparing a water insoluble gel composition according to claim 1, wherein the water soluble polysaccharide is at least one selected from the group consisting of hyaluronic acid, hyaluronate, poly-γ-glutamic acid, poly-γ-glutaminate, agar, alginic acid, alginate, carrageenan, furcellaran, pectin, arabic gum, karaya gum, tragacanth gum, ghatti gum, guar gum, locust bean gum, psyllium seed gum, gleatin, chitin, dextran, xanthan gum, chitosan, chondroitin-4-sulfate, chondroitin-6-sulfate and starch.

6. The method for preparing a water insoluble gel composition according to claim 1, wherein the epoxy cross-linking agent is used in an amount of 0.01-60 parts by mole per mole of the hydroxyl groups in the water soluble polysaccharide.

7. The method for preparing a water insoluble gel composition according to claim 1, wherein the epoxy cross-linking agent is at least one selected from the group consisting of epichlorohydrin, epibromohydrin, 1,4-butandiol diglycidyl ether, ethylene glycol diglycidyl ether, 1,6-hexanediol diglycidyl ether, propylene glycol diglycidyl ether, polyethylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, trimethlypropane polyglycidyl ether, 1,2-(bis(2,3-epoxypropoxy)ethylene, pentaerythritol polyglycidyl ether and sorbitol polyglycidyl ether.

8. The method for preparing a water insoluble gel composition according to claim 1, wherein the alkaline compound is a compound comprising an alkali metal including sodium, potassium, calcium and lithium.

9. A water insoluble gel composition obtained by the method as defined in claim 1.

10. The water insoluble gel composition according to claim 9, which comprises 1-20 wt % of the water insoluble gel based on the total weight of the composition.

11. The water insoluble gel composition according to claim 9, which is transparent when the water insoluble gel has a swelling degree of 30-200, is translucent and milky white when the water insoluble gel has a swelling degree of 10 to less than 30, and is opaque and white when the water insoluble gel has a swelling degree of 2 to less than 10.

12. The water insoluble gel composition according to claim 9, wherein 70-99 wt % of the originally introduced composition remains as a water insoluble gel, when the composition is introduced to a phosphate buffer solution having a pH of 6.5-7.5, swelled and pressure sterilized.

13. The water insoluble gel composition according to claim 12, which has a weight after swelling corresponding to 2-200 times of the dry weight of the water insoluble gel remaining after the pressure sterilization.

* * * * *